(12) United States Patent
Ng et al.

(10) Patent No.: US 6,837,312 B2
(45) Date of Patent: Jan. 4, 2005

(54) CORER-GRINDER

(76) Inventors: Tze Cheun Ng, Room 1605, Island Centre, No. 1, Great George St., Causeway Bay (HK); Kai Leung Yung, Room 1605, Island Centre, No. 1, Great George St., Causeway Bay (HK); Chun Ho Yu, Room 1605, Island Centre, No. 1, Great George St., Causeway Bay (HK); Chiu Cheung Chan, Room 1605, Island Centre, No. 1, Great George St., Causeway Bay (HK)

( * ) Notice: Subject to any disclaimer, the term of this patent is extended or adjusted under 35 U.S.C. 154(b) by 180 days.

(21) Appl. No.: 10/133,215

(22) Filed: May 8, 2002

(65) Prior Publication Data

US 2003/0209092 A1 Nov. 13, 2003

(51) Int. Cl.[7] ................... E21B 11/02; E21C 51/00; G01N 1/08
(52) U.S. Cl. .................. 175/20; 175/58; 175/249; 73/864.44; 73/864.45
(58) Field of Search .................. 175/20, 58, 249, 175/244, 403; 73/864.44, 864.45, 864.42, 864, 864.41

(56) References Cited

U.S. PATENT DOCUMENTS 4,354,558 A * 10/1982 Jageler et al. ............... 175/45
4,594,885 A * 6/1986 Rodger ........................ 73/84

\* cited by examiner

*Primary Examiner*—David Bagnell
*Assistant Examiner*—Giovanna Collins
(74) *Attorney, Agent, or Firm*—Blaney Harper; Russell O. Paige; Jones Day

(57) ABSTRACT

A novel corer and grinder apparatus suitable for interplanetary travel and extraplanetary operation is disclosed. The corer grinder composes a claw element attached to a shaft coupled to a motor. A second motor compresses a spring forcing against a hammer unit that constitute the majority of the unit's mass. On release the energy stored in the compressed spring converts into momentum of the hammer unit that strikes against the claw element releasing the impact energy directly to the cutting end for cutting. The direction of the energy released is modified by an impact platform to produce a horizontal chipping action to aid cutting. The claw element further comprises a pair of semi-cylindrical claw elements that separate upon rotation of the shaft in a first direction, easing collection of core samples. The semi-cylindrical claw elements join upon rotation of the shaft in the opposite direction, thereby grasping the core sample during removal from the material being sampled. Operation of a third motor during rotation of the shaft extends and orbitally moves an X-Y table that permits the corer grinder to operate as a surface grinder over a relatively large surface area. Floating couplings of the claw elements minimize the transmission of vibration to internal elements of the corer grinder.

4 Claims, 5 Drawing Sheets

CORER-GRINDER

BACKGROUND OF THE INVENTION

This invention relates generally to a sampling and coring device for conducting geologic field work. More particularly, this invention relates to a low mass, multifunctional geologic sampling and coring device for interplanetary travel and for use in an extraplanetary environment, specifically Mars. Such extraplanetary operation includes collection of soil and rock samples in an uncontaminated, unchanged form at Martian ambient conditions.

Modern scientific research methods, particularly those involving handling and analysis of small objects, are conducted with the consensus that properly designed tweezers can greatly extend the functionality of the human hands. This consensus is demonstrated by the fact that tweezers are the most common hand instruments used in scientific laboratories. This fact was central to the development of the Space Holinser Forceps System, which has helped astronauts work under zero or micro gravity. The Space Holinser Forceps system contains more than 70 inter-connectable components and over 100 functional combinations. This system was found suitable for gripping objects of any shapes and up to 7.75 in. (20 cm.) in size under zero gravity or micro-gravity environment. Variants of the system have been used in the Russian space station MIR by the Russian astronauts manning the space station. The present invention is an extension of that concept, specifically applied to geologic sampling and coring.

After the series of Vikings and the Pathfinder missions, scientists concluded that the most scientifically and geologically useful secrets of Mars are undoubtedly hidden under the rind of its rocks or beneath its soil, thus indicating where the search for life on Mars should begin.

However, this created a contingent need for a device that could collect manipulate and analyze the Martian rocks and soil, while meeting the unique requirements of extraplanetary operation. The stringent requirements of interplanetary exploration include a requirement that the device be able to self-adapt to the Martian environment, survive large temperature fluctuations, and work in ambient temperatures as low as minus 80 degrees Celsius. Furthermore, a sampling and coring device suitable for interplanetary travel must be capable of surviving the high impulse shocks and accelerations on take-off and landing. Operationally, the device must be highly reliable, able to operate in a vacuum, and it must function with no outgassing. Due to the nature of space flight the device must have minimum mass and be anti-jamming, i.e. it must be capable of continuous operation despite physical obstructions, whether those obstructions are external or internal to the device.

Other functional requirements of such a machine include coring into hard igneous rocks with a power supply of less than 3 watts, a total mass of the unit not more than 400 gm. and a reaction force of less than 1 Kg. Vibration during operation must not be allowed to transmit back to the arm large enough to disturb the other instruments such as the cameras and microscope. These functional requirements plus the environmental requirements have resulted in many unique design features being developed in the machine that will be useful not only for interplanetary explorations but also for other use on earth.

There are analogies in the prior art, particularly in the field of underwater sampling. For example, U.S. Pat. No. 5,559,295 to Sheryll discloses an underwater sampling method and apparatus for collecting uncontaminated samples from an underwater environment at high in situ pressure. However, underwater sampling apparatus require many bulky features to permit the apparatus to function at relatively high ambient pressures. These features, such as thick-walled steel construction and—in the case of the Sheryll device—means for injecting fluids at high pressure to equalize internal and ambient pressures, add bulk and weight that make interplanetary transportation unfeasible or prohibitively expensive. Other limitations of the prior art are exemplified by U.S. Pat. No. 4,317,490 to Milberger et al., which relates to an underwater sampling device in which a sample tube and ball valve are operated from the water surface via a drill string. Such mechanical remote control systems as disclosed in the Milberger et al. device are naturally impossible for interplanetary sampling operations.

OBJECTS OF THE INVENTION

In order to overcome the above-mentioned shortcomings of the related art, it is an object of the present invention to provide an improved device for geologic sampling and coring.

It is another object of the present invention to provide a sampling and grinding device that is capable of grinding targeted samples to expose subsurface features.

It is a further object of the present invention to provide an improved sampling, and coring device that is suitable for interplanetary travel and extraplanetary operation.

It is yet another object of the present invention to provide a sampling and coring device that minimizes vibration. It is a further object of the present invention to cut into rocks with very low backing force.

It is a further object of the present invention to provide a sampling and coring device that transmits a high percentage of its total mass to the cutting elements used in coring operations.

Another object of the present invention is to provide a coring and grinding apparatus with a corer cutting element that opens while cutting the sample and that closes to grip the sample for removal.

A further object of the present invention is to ensure that most of the samples collected after coring are material from the required depth.

SUMMARY OF THE INVENTION

Figure 1:
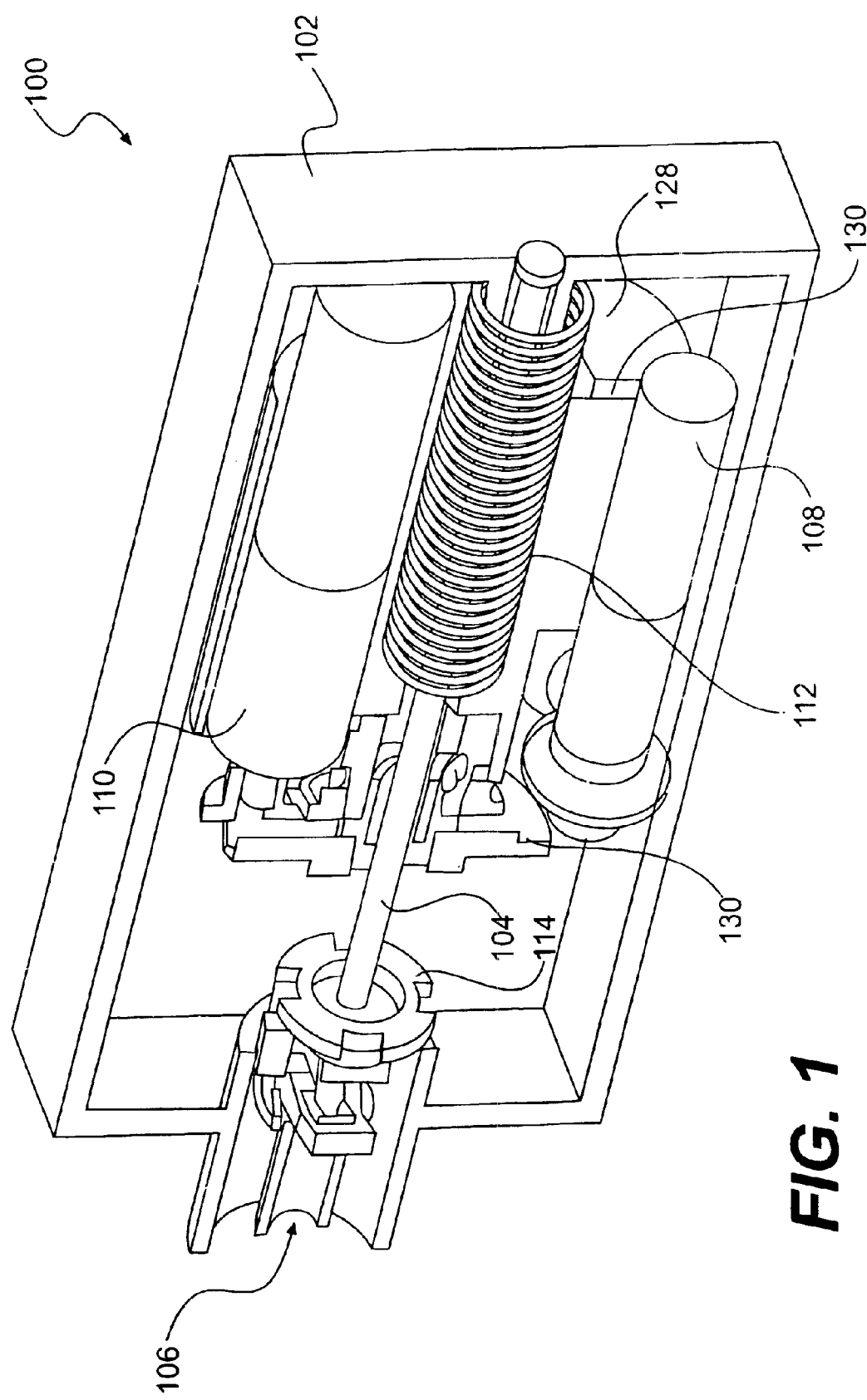
FIG. 1 is a cut open orthogonal illustration of a corer assembly of the corer grinder device of the present invention.

The present invention adds the function of gripping, as with tweezers or forceps, to the coring and automatic extraction of samples from the inside of rocks. Embodiments of the invention weigh no more than one pound (450 gm.) and can be used to core into rocks with a backing force of no more than 4.5 pounds (20 newtons), which is most suitable for interplanetary sampling expeditions where mass of the instrument and the lack of backing force are of prime consideration. The embodied coring head has a unique design that cores into rocks to a depth of 0.4 inches (10 mm) and can grip the sample by closing its jaws hence reducing the diameter of the tip to eliminate any chances of jamming, a vital feature when remote autonomous robotics is concerned. The same embodiment can also grind rock surface to a diameter of 1.5 inches (40 mm) and 0.1 inch (3 mm) in depth. This design has been chosen by the European Space Agency for its "Mars Express" mission that extract samples inside rocks and underneath the surface of the planet Mars for in-situ analysis to search for signs of life. Variants of this design will also be useful on earth for applications such as gas and oil exploration.

DETAILED DESCRIPTION OF THE PREFERRED EMBODIMENTS

FIG. 1 is an orthogonal view of the corer sampler element, represented generally as 100, of the corer grinder apparatus of the present invention. Housing 102 encases a shaft 104 that is connected to claw assembly 106. Shaft 104 is located through the middle of hammer unit 130 which houses the drive motor 108 and coupling motor 110. Both motors are positioned proximate one end of housing 102 that is opposite the end of housing 102 proximate the claw assembly 106. During coring, both drive motor 108 and coupling motor 110 inside the housing 102 will rotate. Coupling motor 110 turns a coupling that transmits the rotary motion to shaft 104 which extends from the motor end of housing 102, passing through coil strike spring 112, beyond which shaft 104 connects to claw assembly 106. Drive motor 108 rotates a large gear 128 (not shown) that lifts the entire hammer unit 130 and simultaneously compresses spring 112. As persons of ordinary skill will recognize, means other than a gear may be used to cause the axial movement of shaft 104. Upon a predetermined travel of shaft 104, a ratcheted stop disengages to release the spring and accelerate the hammer unit 130 under the force of the spring to strike against the impact platform of the claw assembly 106 which in turn directs the impact energy towards the soil or rock being sampled (not shown).

Figure 2:
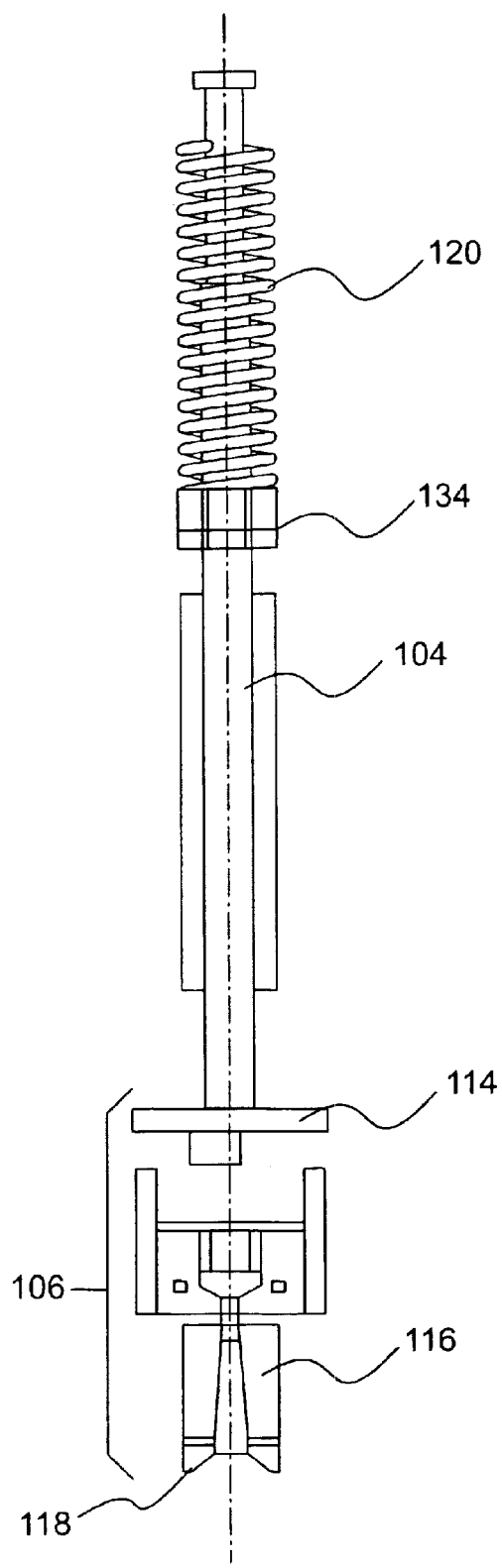
FIG. 2 is an illustration of a claw assembly of the corer grinder of the present invention.

Referring now to FIG. 2, the claw assembly is shown in more detail. Contact force spring 120 is located on the top of the claw assembly, and lies interior to, and parallel with, strike spring 112. Contact force spring 120 provides the necessary pressure for the coring tip 118 to maintain contact with the rock or soil being sampled during coring or grinding. Ring 134 is affixed to shaft 104 and serves as a stop for contact force spring 120.

On impact the kinetic energy of the hammer unit 130 is transmitted through impact platform 114 to coring cutting tip 118 for cutting the rock or soil being sampled. Coring cutting tip 118 is connected to a pair of semicylindrical claw elements 116 that are configured as shown whereby on forward motion of shaft 104, the claw elements 116 are forced slightly apart axially, thus causing the coring cutting tip 118 to widen its diameter of operation. As also can be seen in FIG. 2, upon reverse motion of shaft 104, claw elements 116 are drawn towards each other along the cylindrical axis of shaft 104, which permits corer cutting tip 118 and claw elements 116 to grip the sample obtained through the coring operation. The function of the widening of the cutting tip's operational diameter aids in the gathering of the sample material by coring cutting tip 118. Similarly, the closing of claw elements 116 upon reverse motion of shaft 104 aids in the retention of the sample obtained subsequent to its acquisition by coring cutting tip 118.

When the coring action reaches the required depth, the coupling motor 110 rotates in the reverse direction, whereupon claw elements 116 are drawn together, causing the coring cutting tip 118 to close and grasp the rock sample. Once the coring cutting tip 118 containing a rock or soil sample is completely retracted from the rock or soil being sampled, forward rotation of shaft 104 will again force claw elements 116 apart axially, thereby causing coring cutting tip 118 to open and release the rock or soil sample acquired.

Figure 3:
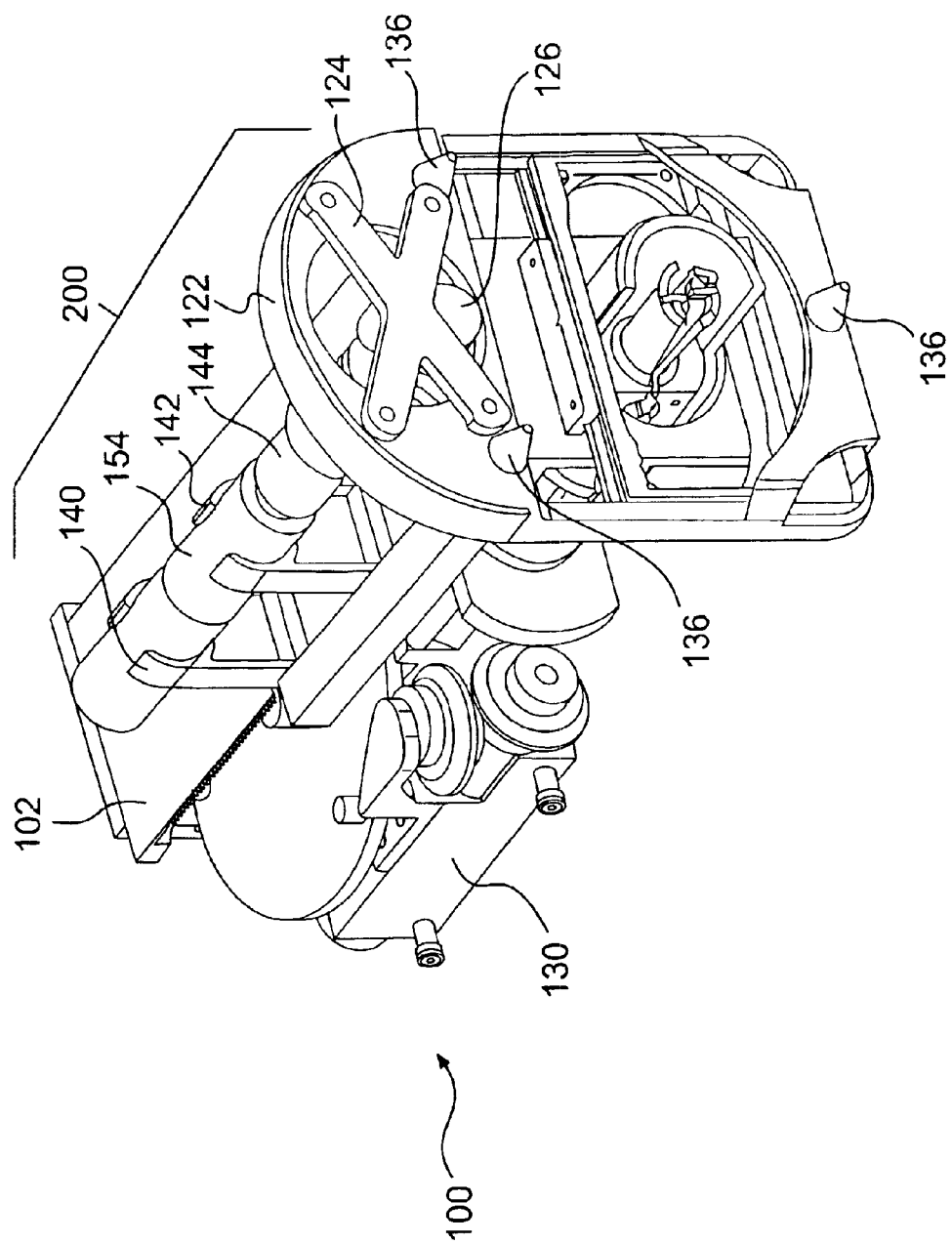
FIG. 3 is a cut open orthogonal illustration of the corer grinder device with the grinding attachment installed.

In a preferred embodiment, the corer grinder of the present invention can be used for grinding the surface of a rock to be sampled, typically prior to cutting a core sample as described above. Such grinding may also be desirable for in situ analysis or for observation of subsurface soil or rock. FIG. 3 shows a cutaway view of the corer sampler 100 with an attached grinder table assembly 200 which comprises as shown X-Y table 122, motor/gearbox asssembly 154, bushing/nut mechanism 132, and brackets 140, 142 and 144. Cross-bracket 124 is attached at its perimeter to the underside of X-Y table 122, and cross-bracket 124 is attached at its center to planetary gear 126. Planetary gear 126 is connected to motor/gearbox asssembly 154 and bushing/nut mechanism 132 as shown in FIG. 4.

Figure 4:
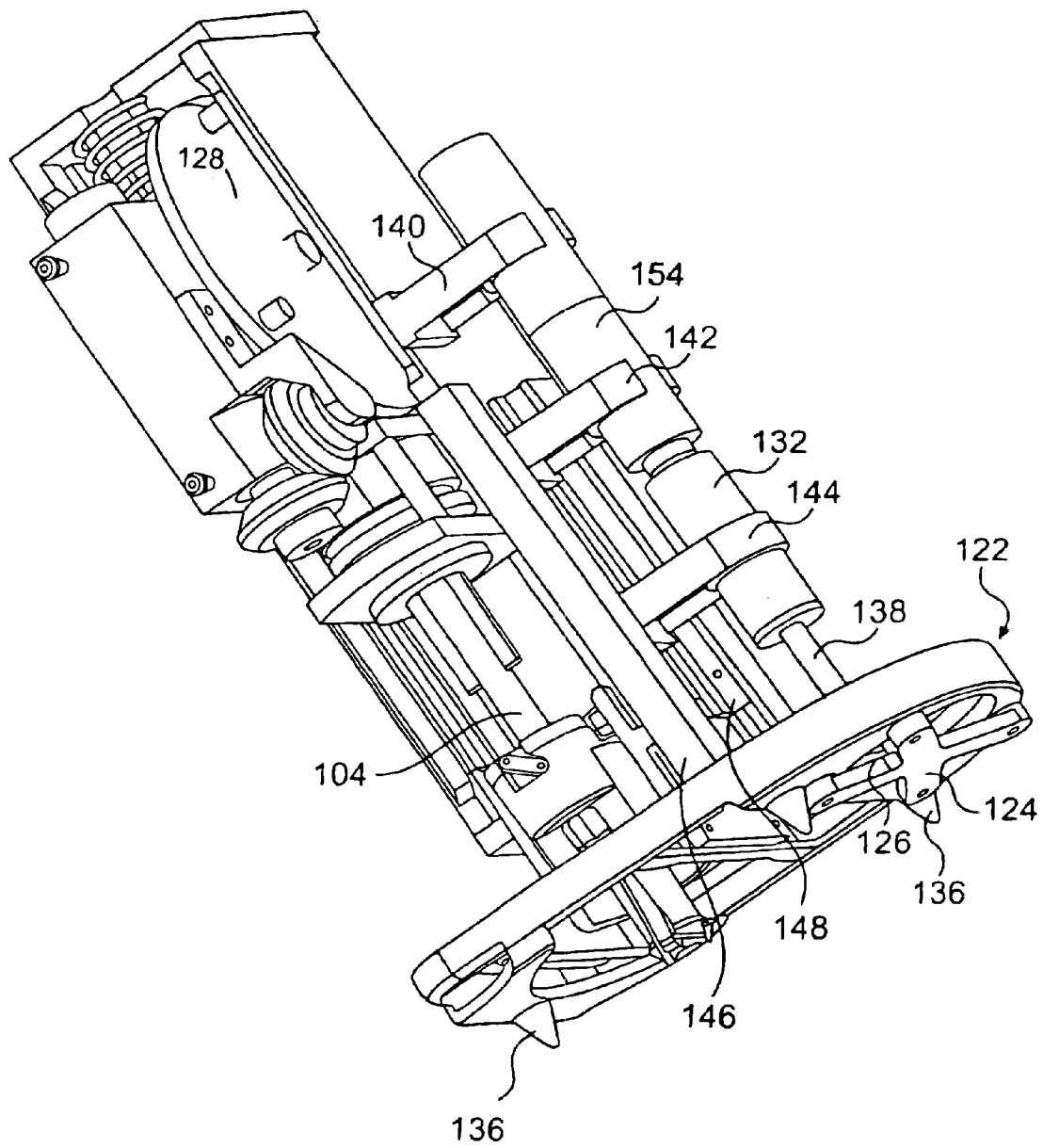
FIG. 4 is a cut open orthogonal illustration of the corer grinder device with the X-Y table fully extended ready for grinding operation.

Further detail of the corer grinder with the attached grinder table assembly 200 is shown in FIG. 4. Cross-bracket 124, attached at its perimeter to X-Y table 122, is connected at its center to planetary gear 126, which is axially coupled to motor/gearbox asssembly 154 by leadscrew 138 and bushing/nut mechanism 132. Motor/gearbox asssembly 154 operates to extend X-Y table 122 in the axial direction of motor/gearbox asssembly 154, which in the preferred embodiment shown is cylindrical. Motor/gearbox asssembly 154 is affixed at one end to corer housing 102 by gearbox bracket 140, and is supported at the other end by intermediate bracket 142. Bushing/nut mechanism 132 is supported by bushing bracket 144 which in turn is immovably secured to housing 102. Motor 140 and gearbox bracket 142 are immovably secured to corer housing 102. As persons of ordinary skill in the art will appreciate, the track mechanism 148 may be a separate component, or it can be integrated into the design of corer housing 102. Further, brackets 146 which is an integral part of the mechanism that link to the X-Y table 122 may slide along track mechanism 148 directly. As motor/gearbox asssembly 154 operates, bushing/nut mechanism 132 and leadscrew 138 are driven axially. Extension of the table motor and gearbox asssembly 154 operates to extend the X-Y table 122 so as to space the corer housing 102 and its connected components away from the surface to be ground during grinding operation.

Further in FIG. 4, the corer grinder of the present invention is shown with the X-Y table 122 extended and ready for the grinding operation. The three prongs 136 on the underside of the X-Y table 122 are for stably positioning the corer-grinder assembly on the material to be ground. In a preferred embodiment, the prongs 136 have sharp points for adhering to a variety of surfaces. For grinding according to the present invention, the coring action described above is actuated but with the shaft 104 extended so that claw assembly 106 extends beyond housing 102 during operation. During grinding the table motor (not shown) included in motor/gearbox assembly 154 operates and in a preferred embodiment rotates leadscrew 138 thereby driving the planetary gear 126 that in turn drives the X-Y table 122 to move in a generally circular or geometrically eccentric pattern parallel to the plane of the surface to be ground. Such orbital motion of X-Y table 122 causes corer sampler element 100 together with the cutting tip 118 to follow a shifted elliptical path across the surface of the material to be sampled.

Drag produced as a result of the corer tip 118 moving along the rock surface is also minimized by a hopping action of the claw assembly 106. This hopping action is generated by the hammer body 130 as it raises to its top end and hits against ring 134 (FIG. 2) along shaft 104 thereby lifting the whole claw assembly 106 with it.

In a preferred embodiment of the corer grinder of the present invention, as the action of the corer cutting tip 118 removes the surface of the sample material, the shifting elliptical path gradually moves the corer cutting tip 118 to cover an area to be ground by the corer cutting tip, which is in the preferred embodiment a circular area of approximately 1.5 inches (40 mm) in diameter. On completion of grinding, table motor and gearbox asssembly 154 operates in the reverse direction to retract X-Y table 122, and to return the claw assembly 106 to a position ready for repeating the coring action.

A novel feature of this grinding action is the use of a single motor and simple passive mechanism, both features embodied in table motor and gearbox asssembly 154, to achieve extension and retraction of the X-Y table 122 as well as lateral orbital movement of the X-Y table 122 to articulate the gradually shifting round elliptical path for the corer tip 118 to grind across the surface of the material to be ground. The extension and retraction of the X-Y table 122 is achieved by a leadscrew 138 and nut mechanism 132 that incorporates friction free end stops inside bushing/nut mechanism 132 (not shown) in a manner familiar to those of ordinary skill in the art. Leadscrew 138 in turn connects to the arm of the planetary gear 126 for the orbital sweeping movement of the X-Y table 122.

Figure 5:
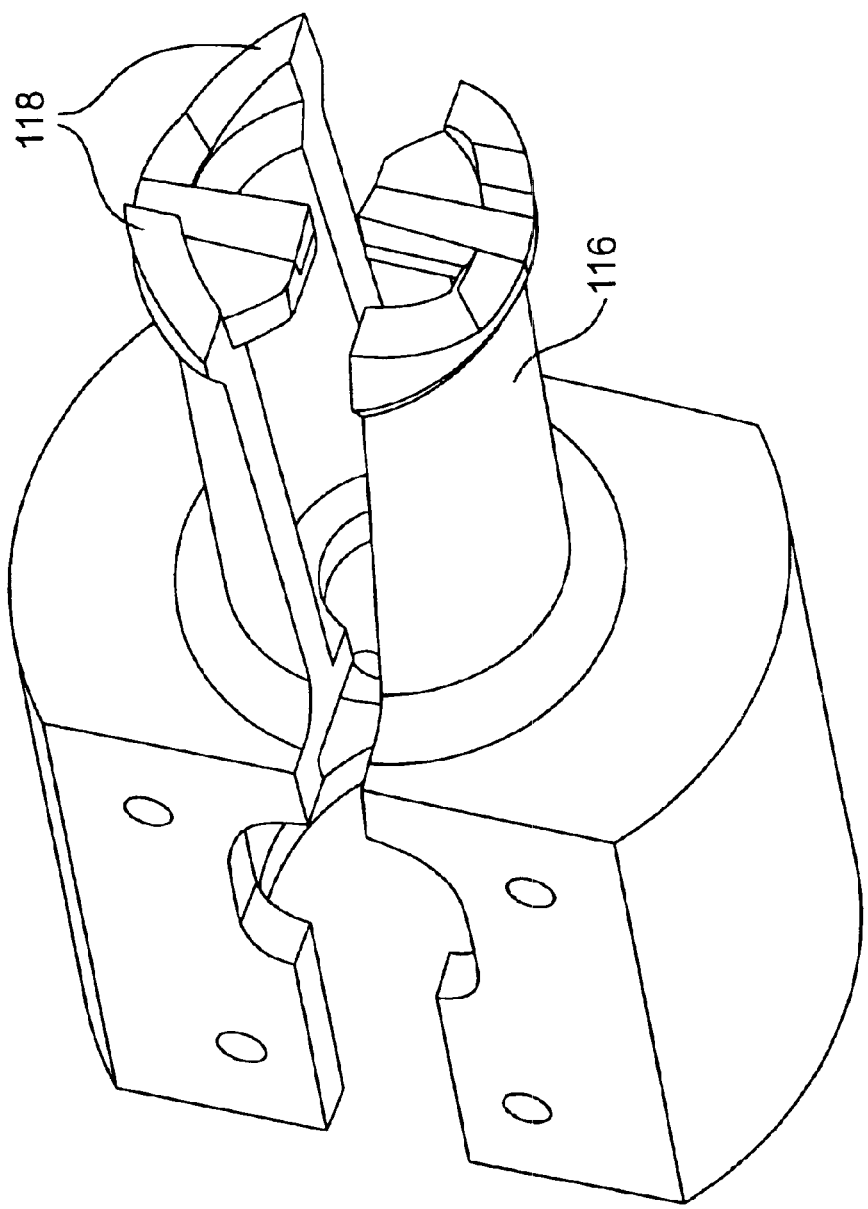
FIG. 5 shows a close up view of the coring tip.

A further novel design of this corer is the cutting teeth, as shown in FIG. 5, of the core cutting tip 118 that directs the freshly cut material towards the centre of the generally semicylindrical claw elements 116. As the freshly cut material builds up in the centre of claw elements 116, it pushes previously cut old materials up the centre of claw elements 116, finally spilling out to the surface through the gaps between the claw elements. This feature of the preferred embodiment of the present invention ensures that the material that is gripped by the claw elements 116 at the end of a coring operation will consist mainly of materials from the desired depth.

A novel element of the corer grinder of the present invention is the use of most of the mass of the apparatus of the present invention, including the mass of coupling motor 110 and drive motor 108 are converted into kinetic energy in the hammer unit 130 by coil spring 112 and released directly to corer cutting tip 118 on the sample material during impact of the hammer unit 130 on the impact platform 114. Corer assembly 106 is designed to include an impact platform 114 arranged so that the impact energy released to the corer tip 118 is directed in an orientation so as to chip away the rock being sampled at an angle to the surface.

Reduction of the impact vibration from feeding back to the arm is achieved by a floating design of the corer cutting tip 118 so that it is not connected rigidly to any part of the main body of the corer grinder 100.

Another novel element of the corer grinder of the present invention is in the transmission of rotational torque from the motor on the hammer body to the shaft while maintaining the very low friction between the hammer and the shaft when the hammer is moving along the shaft.

Although the invention is described and illustrated with respect to the exemplary embodiments thereof, it should be understood by those skilled in the art that the foregoing and various changes, omissions and additions may be made without departing from the spirit and scope of the invention

We claim:

1. A corer grinder comprising:
   a shaft having a proximal end and a distal end;
   a coupling motor operatively connected to said shaft;
   a coil spring connected to said proximal end of said shaft;
   a drive motor operatively connected to said spring;
   a claw assembly fixedly connected to said shaft at said distal end whereby operation of said drive motor compresses said spring, and whereby release of said spring transmits the potential energy of said compressed spring and the inertia of said coupling motor and said drive motor and said claw assembly;
   said claw assembly further comprising a first claw element and a second claw element; and
   said first and second claw elements flexibly connected to said shaft.

2. A corer grinder as in claim 1, wherein rotation of said shaft in a first direction causes said first claw element and said second claw element to separate.

3. A corer grinder as in claim 1, wherein rotation of said shaft in a second direction causes said first claw element and said second claw element to join.

4. A corer grinder as in claim 1, further comprising a cutting tip, said cutting tip comprising:
   an impact platform for directing kinetic energy from said shaft directly to said cutting tip.

* * * * *